United States Patent
Anderson et al.

(10) Patent No.: US 11,577,028 B2
(45) Date of Patent: Feb. 14, 2023

(54) SYRINGE WITH A BIDIRECTIONAL PLUNGER ADVANCING MECHANISM FOR A MICRO-DOSING SYRINGE PUMP

(71) Applicant: BECTON, DICKINSON AND COMPANY, Franklin Lakes, NJ (US)

(72) Inventors: Nicholas Anderson, Whitman, MA (US); Andrew Beaupre, Somerville, MA (US)

(73) Assignee: Becton, Dickinson and Company, Franklin Lakes, NJ (US)

(*) Notice: Subject to any disclaimer, the term of this patent is extended or adjusted under 35 U.S.C. 154(b) by 276 days.

(21) Appl. No.: 17/153,172

(22) Filed: Jan. 20, 2021

(65) Prior Publication Data
US 2022/0226581 A1    Jul. 21, 2022

(51) Int. Cl.
*A61M 5/315*    (2006.01)
*A61M 5/145*    (2006.01)

(52) U.S. Cl.
CPC ....... *A61M 5/31536* (2013.01); *A61M 5/3156* (2013.01); *A61M 5/31528* (2013.01); *A61M 5/31545* (2013.01); *A61M 5/31548* (2013.01); *A61M 2005/14506* (2013.01)

(58) Field of Classification Search
CPC .......... A61M 5/31536; A61M 5/31525; A61M 5/31526; A61M 5/31528; A61M 5/31533; A61M 5/31565; A61M 5/31576; A61M 5/31578; A61M 5/31583; A61M 5/31586; A61M 3/14546; A61M 5/3153; A61M 5/31548; A61M 5/3155; A61M 5/31551; A61M 5/31555; A61M 5/3158; A61M 5/31581; A61M 5/31593; A61M 5/31595; A61M 2005/31588; A61M 2005/14506; A61M 2005/3154
See application file for complete search history.

(56) References Cited

U.S. PATENT DOCUMENTS 4,050,459 A * 9/1977 Sanchez ............ A61M 5/31595
                                                    604/210
4,475,905 A * 10/1984 Himmelstrup .... A61M 5/31551
                                                    604/263
4,749,109 A    6/1988 Kamen
(Continued)

FOREIGN PATENT DOCUMENTS

CN    107 666 930 A    2/2018

*Primary Examiner* — Nathan R Price
*Assistant Examiner* — Justin L Zamory
(74) *Attorney, Agent, or Firm* — Dickinson Wright PLLC

(57) ABSTRACT

Disclosed is a syringe for a micro-dosing syringe pump. The syringe includes a reservoir having an outlet port; a plunger having a track, with the plunger received inside a portion of the reservoir; a plunger driver comprising a gear connected to one end of a shaft and a pin located adjacent an opposite end of the shaft, with the plunger driver received inside the plunger and with the pin located inside and engaging the track. In use, rotation of the gear in a first direction advances the plunger into the reservoir a first distance as the pin travels in the track and rotation of the gear in a second direction opposite the first direction advances the plunger a further distance into the reservoir as the pin travels in the track. The design prevents excess dosing in a runaway motor failure.

20 Claims, 5 Drawing Sheets

(56) References Cited

U.S. PATENT DOCUMENTS

| | | | |
|---|---|---|---|
| 9,022,993 B2* | 5/2015 | Dasbach | A61M 5/31593 |
| | | | 604/211 |
| 10,149,947 B2 | 12/2018 | Bayer et al. | |
| 2002/0077598 A1* | 6/2002 | Yap | A61M 39/12 |
| | | | 128/DIG. 10 |
| 2013/0110054 A1* | 5/2013 | Raab | A61M 5/31541 |
| | | | 604/224 |

* cited by examiner

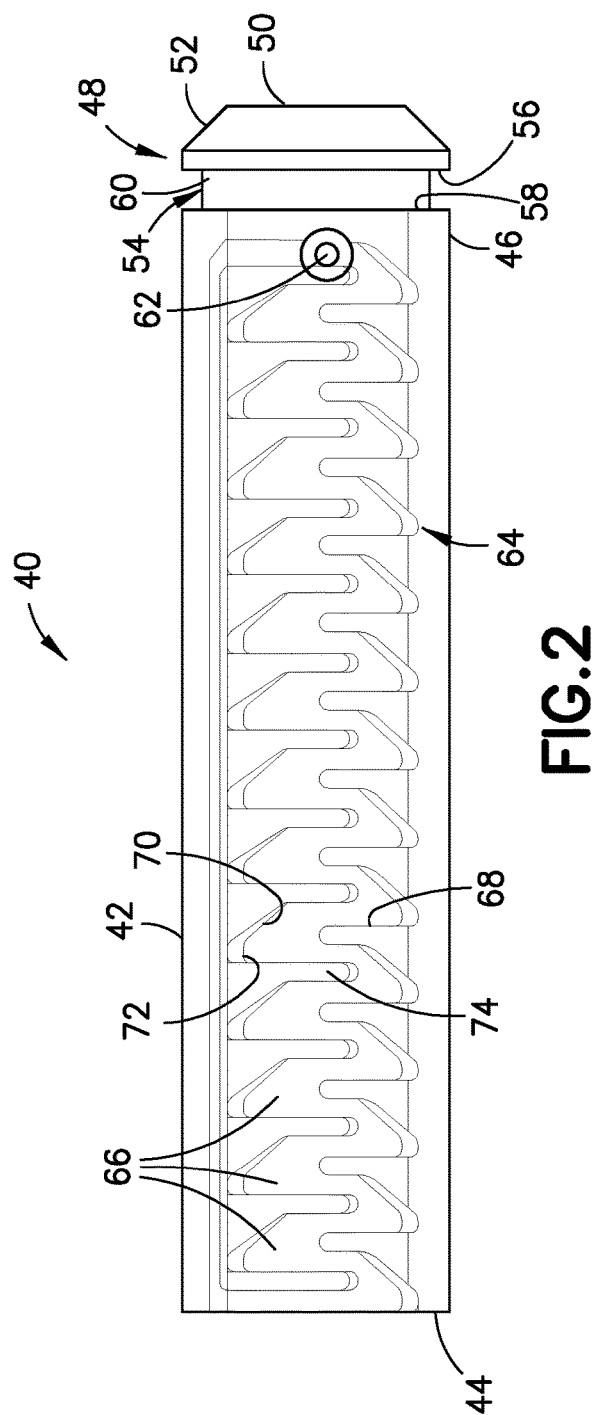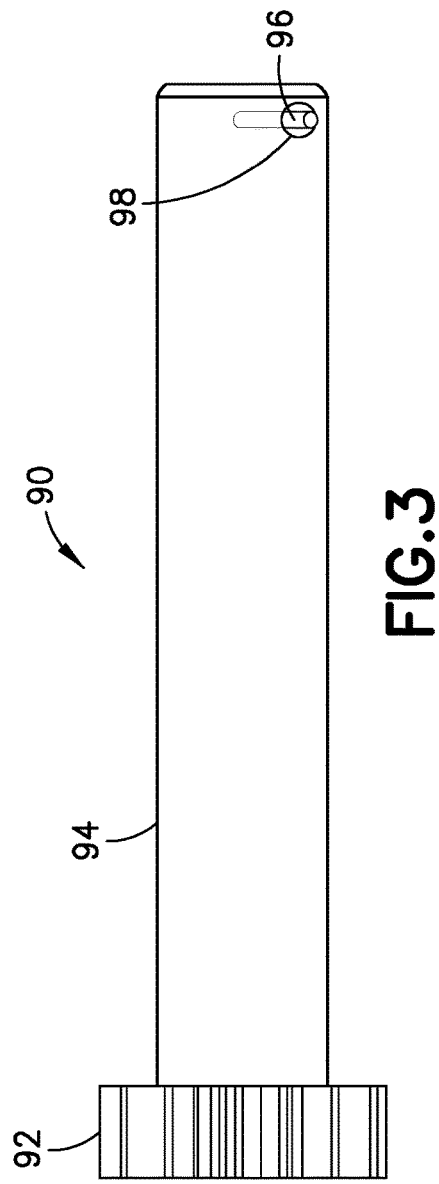

SYRINGE WITH A BIDIRECTIONAL PLUNGER ADVANCING MECHANISM FOR A MICRO-DOSING SYRINGE PUMP

CROSS-REFERENCE TO RELATED APPLICATIONS

NONE.

STATEMENT REGARDING FEDERALLY SPONSORED RESEARCH

NONE.

STATEMENT REGARDING JOINT DEVELOPMENT AGREEMENT

NONE

REFERENCE TO SEQUENCING LISTING, TABLE OR COMPUTER PROGRAM LISTING

NONE.

STATEMENT REGARDING PRIOR DISCLOSURES BY THE INVENTOR OR A JOINT INVENTOR UNDER 33 C.F.R 1.77(B)(6)

NONE.

FIELD OF THE DISCLOSURE

This present disclosure relates generally to a syringe for a micro-dosing syringe pump, and more particularly to a syringe having a bidirectional advancement mechanism and a runaway pump motor safety feature.

BACKGROUND OF THE DISCLOSURE

This section provides background information which is not necessarily prior art to the inventive concepts associated with the present disclosure.

Micro-dosing syringe pumps are known in the art and often used to deliver medicaments such as insulin, other hormones, chemotherapy medicaments, antibiotics and pain relievers just to name a few. These devices include a syringe generally comprising a reservoir, a plunger and a means to drive the plunger into the reservoir to deliver the medicament to a patient. Often times the means to drive the plunger comprises a telescoping set of screw drives that telescope outward as an end gear is driven in a rotational manner in one direction. Other systems use a screw-threaded rod that is rotated to drive a nut that is connected to the plunger, with rotation of the rod driving the nut upward and the plunger into a reservoir. Other systems use a scissoring system to drive a plunger into a reservoir. In general, for all of these systems the mechanism usually involves rotation of a part to drive the plunger and the rotation is always in the same direction.

One issue with all of these prior art plunger driver mechanisms is that they need complicated methods to address the issue of over-dosing. Such an issue can arise when a runaway motor event occurs. In such an event the motor, which drives the plunger through one of the aforementioned mechanisms, continues to run after delivery of the intended dose and thus the dosing continues and the patient can be over-dosed.

It is desirable to provide a plunger driver mechanism that avoids the problems of a runaway motor event and does so in a cost effective and simple manner. The present invention provides an elegant, mechanical, always "on" guard against runaway motor events. It also provides for accurate and repeatable dosing in a micro-dosing syringe pump system.

SUMMARY OF THE DISCLOSURE

This section provides a general summary of the present disclosure and is not intended to be interpreted as a comprehensive disclosure of its full scope or all features, aspects and objectives.

One aspect of the present invention is a syringe for a micro-dosing syringe pump. The syringe comprising: a reservoir having an outlet port; a plunger having a track, with the plunger received inside a portion of the reservoir; a plunger driver comprising a gear connected to one end of a shaft and a pin located adjacent an opposite end of the shaft, with the plunger driver received inside the plunger with the pin located inside and engaging the track; and whereby rotation of the gear in a first direction advances the plunger into the reservoir a first distance as the pin travels in the track and rotation of the gear in a second direction opposite the first direction advances the plunger into the reservoir a second distance as the pin travels in the track with the second distance being greater than the first distance.

Another aspect of the present disclosure is to provide a syringe for a micro-dosing syringe pump. The syringe comprising: a reservoir having an outlet port; a plunger having a track, the track comprising a plurality of slots, each of the slots comprising a straight run, a camming run and an end point, and with the plunger received inside a portion of the reservoir; a plunger driver comprising a gear connected to one end of a shaft and a pin located adjacent an opposite end of the shaft, the plunger driver received inside the plunger with the pin located inside and engaging the track; and whereby rotation of the gear in a first direction advances the plunger into the reservoir a first distance as the pin travels in a first of the plurality of slots and rotation of the gear in a second direction opposite the first direction advances the plunger into the reservoir a second distance as the pin travels in a second of the slots with the second distance being greater than the first distance.

These and other features and advantages of this disclosure will become more apparent to those skilled in the art from the detailed description herein. The drawings that accompany the detailed description are described below.

BRIEF DESCRIPTION OF THE DRAWINGS

The drawings described herein are for illustrative purposes only of selected aspects and not all implementations, and are not intended to limit the present disclosure to only that actually shown. With this in mind, various features and advantages of example aspects of the present disclosure will become apparent to one possessing ordinary skill in the art from the following written description and appended claims when considered in combination with the appended drawings, in which:

FIG. 2 shows a plunger for a syringe designed in accordance with the present invention;

FIG. 3 shows a plunger advancer for a syringe designed in accordance with the present invention;

DETAILED DESCRIPTION OF THE DISCLOSURE

Figure 1:
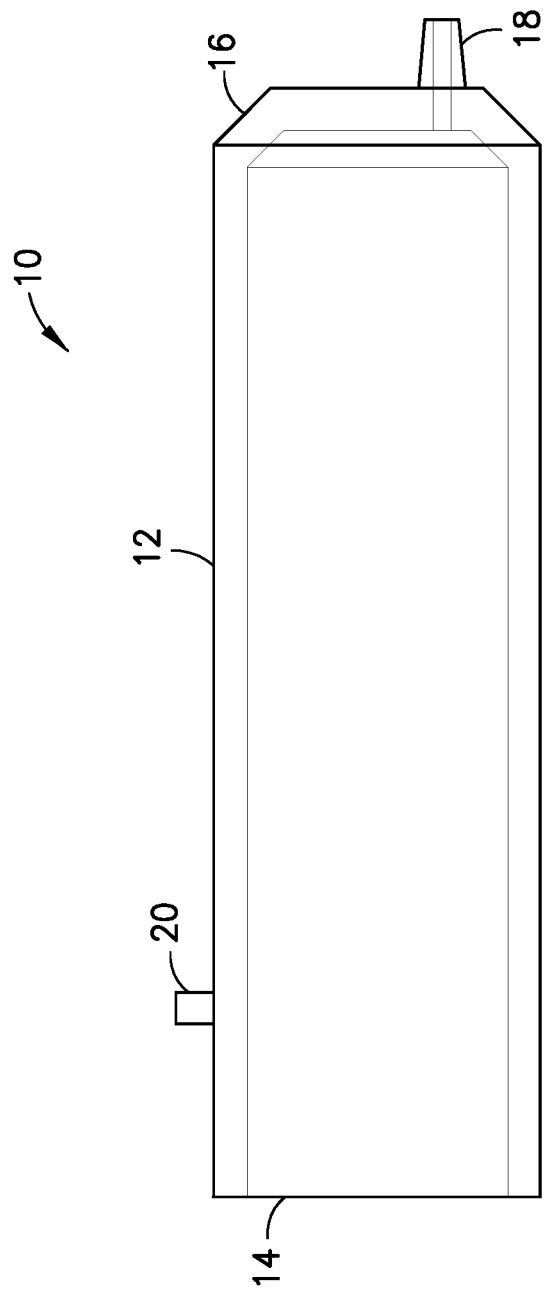
FIG. 1 shows a reservoir for a syringe designed in accordance with the present invention.

In the following description, details are set forth to provide an understanding of the present disclosure.

For clarity purposes, example aspects are discussed herein to convey the scope of the disclosure to those skilled in the relevant art. Numerous specific details are set forth such as examples of specific components, devices, and methods, in order to provide a thorough understanding of various aspects of the present disclosure. It will be apparent to those skilled in the art that specific details need not be discussed herein, such as well-known processes, well-known device structures, and well-known technologies, as they are already well understood by those skilled in the art, and that example embodiments may be embodied in many different forms and that neither should be construed to limit the scope of the disclosure.

The terminology used herein is for the purpose of describing particular example aspects only and is not intended to be limiting. As used herein, the singular forms "a," "an," and "the" may be intended to include the plural forms as well, unless the context clearly indicates otherwise. The terms "comprises," "comprising," "including," and "having," are inclusive and therefore specify the presence of stated features, integers, steps, operations, elements, and/or components, but do not preclude the presence or addition of one or more other features, integers, steps, operations, elements, components, and/or groups thereof. The method steps, processes, and operations described herein are not to be construed as necessarily requiring their performance in the particular order discussed or illustrated, unless specifically identified as an order of performance. It is also to be understood that additional or alternative steps may be employed.

When an element or feature is referred to as being "on," "engaged to," "connected to," "coupled to" "operably connected to" or "in operable communication with" another element or feature, it may be directly on, engaged, connected or coupled to the other element or layer, or intervening elements or features may be present. In contrast, when an element is referred to as being "directly on," "directly engaged to," "directly connected to," or "directly coupled to" another element or feature, there may be no intervening elements or layers present. Other words used to describe the relationship between elements should be interpreted in a like fashion (e.g., "between" versus "directly between," "adjacent" versus "directly adjacent," etc.). As used herein, the term "and/or" includes any and all combinations of one or more of the associated listed items.

Although the terms first, second, third, etc. may be used herein to describe various elements, components, regions, layers and/or sections, these elements, components, regions, layers and/or sections should not be limited by these terms. These terms may be only used to distinguish one element, component, region, layer or section from another region, layer or section. Terms such as "first," "second," and other numerical terms when used herein do not imply a sequence or order unless clearly and expressly indicated by the context. Thus, a first element, component, region, layer or section discussed below could be termed a second element, component, region, layer or section without departing from the teachings of the example embodiments.

For purposes of description herein, the terms "upper," "lower," "right," "left," "rear," "front," "vertical," "horizontal," and derivatives thereof shall relate to the invention as oriented in the FIGS. However, it is to be understood that the present disclosure may assume various alternative orientations and step sequences, except where expressly specified to the contrary. It is also to be understood that the specific devices and processes illustrated in the attached drawings, and described in the following specification are exemplary aspects of the inventive concepts defined in the appended claims. Hence, specific dimensions and other physical characteristics relating to the aspects disclosed herein are not to be considered as limiting, unless the claims expressly state otherwise.

A syringe includes a reservoir, which is also known as the barrel of the syringe. In the present specification and claims, the two terms will be used interchangeably. A typical syringe comprises at least a barrel, a plunger and a plunger driver.

In FIG. 1 a reservoir for a syringe designed in accordance with the present invention is shown generally at 10. The reservoir 10 is generally cylindrical in shape and includes a barrel wall 12 that extends from a first end 14, which is open, to a second end 16, which is closed. The second end 16 includes an outlet port 18 and a medicament is dispensed from the reservoir 10 out through the outlet port 18. The outlet port 18 is ultimately connected to the patient to deliver the medicament to the patient. The reservoir 10 preferably includes an optional fill port 20. Alternatively, the reservoir 10 could be filled through the open end 14 or through the outlet port 18 as known to one of skill in the art. The reservoir 10 is preferably formed in a unitary design. It can be formed from a non-metallic polymeric material such as, for example only, a thermoplastic material. Alternatively, it can be formed from a metallic material such as, for example only, a stainless steel or metal alloy.

In FIG. 2 a plunger for a syringe designed in accordance with the present invention is shown generally at 40. The plunger 40 includes a cylindrically shaped plunger barrel 42 sized to fit closely inside the reservoir 10. This means the external diameter of the plunger 40 is just slightly less than the internal diameter of the reservoir 10. The plunger barrel 42 has an open end 44 opposite a closed end 46. The closed end 46 includes an integral piston 48 having a front face 50 with a sloped rim 52 and a groove 54. The groove 54 includes a front wall 56 opposite a rear wall 58 and a bottom 60. The groove 54 is for receipt of an O-ring and is also known as an O-ring gland. The O-ring is not shown for clarity purposes, however one of skill in the art will readily understand the O-ring is commonly used to provide a seal between the piston 48 and the inner wall of the reservoir 10 to prevent leakage of a medicament from the reservoir 10 when the plunger 40 is advanced into the reservoir 10. One skill in the art will understand the design considerations for selecting an O-ring having the appropriate percent volume fill size for the groove 54, percent compression, percent stretch, and the elastomeric or rubber material forming the O-ring. Also shown in FIG. 2 is an optional through hole 62 passing from outside the plunger barrel 42 into the interior of the barrel 42. The optional through hole 62 is to allow for assembly of the components in one embodiment as will be explained herein. A portion of the interior wall of the plunger barrel 42 includes a track 64. When the optional through hole 62 is present then the track 64 is opposite the through hole 62, as shown. The track 64 comprises a plurality of slots 66, in one embodiment the slots 66 are cut into the interior wall of the plunger barrel 42. AS shown in one embodiment each slot 66 includes a straight run 68, a camming run 70 and an endpoint 72 of the slot 66. The camming run 70 is also known as a camming surface. The camming run 70 is sloped in a direction away from the piston 48 in this embodiment. Each slot 66 connects to an adjacent slot 66 along a length of the track 64. The slots 66 can have a shape other than that shown as would be understood by one of skill in the art. The slots 66 are divided from each other by a separation wall 74. The slots 66 form a zigzag pattern down the track 64. Each zig and each zag is designed to deliver an equivalent dose to each other as described herein. The plunger 40 can also include a bypass track 120, as described in FIG. 6. Although the track 64 is shown as cut into the interior wall of the plunger barrel 42 and not passing through it, this does not have to be the case. The plunger 40 can be formed from a high enough strength material to allow for the track 64 to be cut completely through the plunger barrel 42 wall if desired. The plunger 40 is preferably formed as a unitary piece and can be formed from a polymeric material, such as a thermoplastic or from a metal such as a stainless steel or a metal alloy.

In FIG. 3 a plunger advancer for a syringe designed in accordance with the present invention is shown generally at 90. The plunger advancer 90 includes a gear 92, such as a spur gear, at one end. A shaft 94 is fixed to the gear 92 and opposite the gear 92 is a pin 96 which is received in a through hole 98 in the shaft 94. The pin 96 can be fixed in position using an adhesive or it can be friction fitted into the through hole 98. In one embodiment, the pin 96 is fixed in the through hole 98 prior to assembly of the syringe and in another embodiment it is placed in the through hole 98 during assembly as explained herein. The gear 92 is operatively connected to a motor in a micro-dosing syringe pump, not shown, and the motor is used to rotate the plunger advancer 90 in both a clockwise and a counterclockwise direction. This can be accomplished using one or more drive gears between a driven shaft of the motor and the gear 92 as will be understood by one of skill in the art. This driving of the gear 92 will cause the pin 96 to rotate in a clockwise or counterclockwise direction while staying in the same rotational plane in both directions. The plunger advancer 90 may be formed as a unitary piece including the pin 96 as described herein. The plunger advancer 90 and pin 96 may be formed from a polymeric composition, for example, as a thermoplastic composition. Alternatively, the plunger advancer 90 and pin 96 may be formed from a metal material, for example from a stainless steel of metal alloy.

Figure 4:
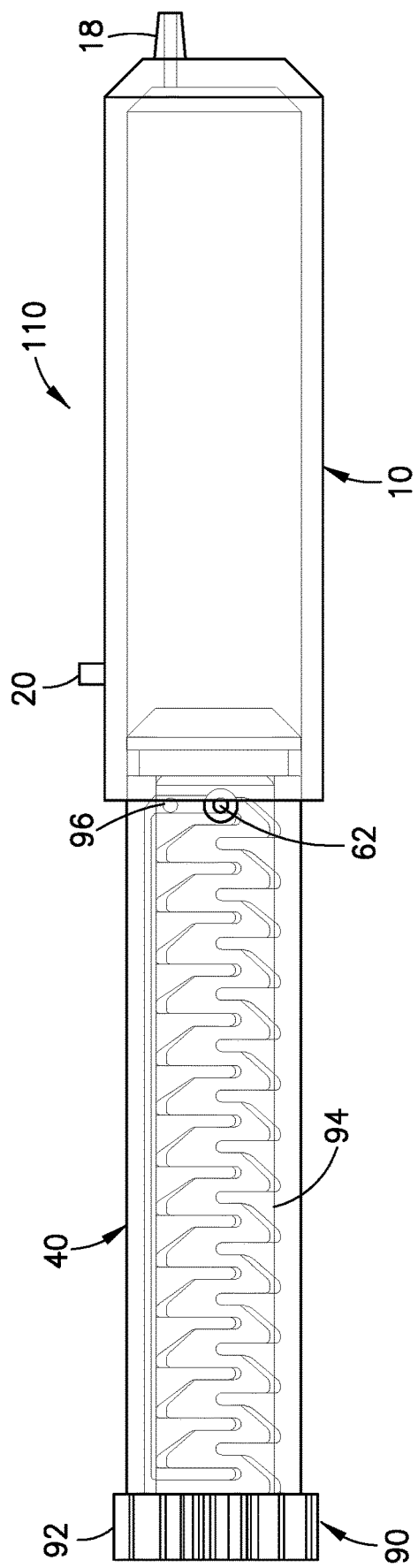
FIG. 4 shows an assembled syringe designed in accordance with the present invention at an initial loaded position using the reservoir of FIG. 1, the plunger of FIG. 2 and the plunger advancer of FIG. 3.

FIG. 4 shows an assembled syringe designed in accordance with the present invention generally at 110. The syringe 110 is shown at an initial loaded position and includes the reservoir 10, the plunger 40 and the plunger advancer 90. The fill port 20, when present, is located such that the reservoir 10 can be filled when the syringe 110 is in this position with the piston 48 located just inside the reservoir 10. In use the syringe 110 will be locate inside a micro-dosing syringe pump, not shown, and will be supported at least at the closed end 16 of the reservoir 10 and at the gear 92. It may also be supported at the open end 14 of the reservoir 10 when located inside the micro-dosing syringe pump. It is supported to prevent any axial or longitudinal movement of the reservoir 10 during use, especially as the plunger 40 is telescoped into the reservoir 10 by the plunger advancer 90. The plunger advancer 90 can rotated in both a clockwise and a counterclockwise direction as driven by the gear 92. The plunger advancer 90 is supported at least at the location of the gear 92 to prevent longitudinal movement of the shaft 94 during its rotation and use. In one embodiment, as discussed above, the plunger 40 includes a through hole 62 opposite the track 64. To assemble the syringe 110 in that embodiment the plunger advancer 90 without the pin 96 is inserted into the open end 44 of the plunger 40. Then the through hole 98 in the shaft 94 is aligned with the through hole 62 in the plunger 40 and the pin 96 can be inserted into the through hole 98 in the shaft 94 using the through hole 62 in the plunger 40. The pin 96 has a length sufficient for it to fully engage the track 64 and ride within the track 64 when it is received in the through hole 98. As shown in FIG. 4, when the syringe 110 is in this position the pin 96 is located in the slot 66 closest to the piston 48.

Figure 5:
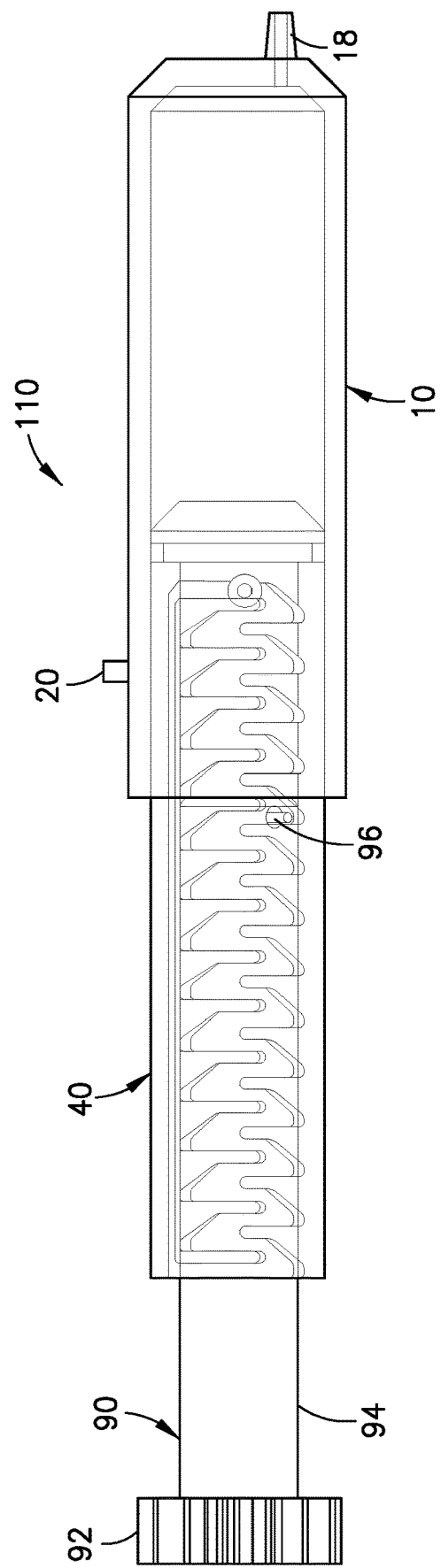
FIG. 5 shows the assembled syringe of FIG. 4 after partial advancement of the plunger into the reservoir.

FIG. 5 shows the assembled syringe 110 of FIG. 4 after partial advancement of the plunger 40 into the reservoir 10. The advancement is caused rotation of the plunger advancer 90 and thereby the pin 96 in an alternative fashion in both a clockwise and a counterclockwise direction. As the rotational direction is alternated the pin 96 rides in the track 64 and engages it, moving from one slot 66 to the next and the plunger 40 is driven into the reservoir 10 and thus medicament is driven out of the outlet port 18. During the entire time the shaft 94 is rotated in each direction the plunger advancer 90 does not change longitudinal position, however the plunger 40 moves longitudinally into the reservoir 10. This movement is better shown in FIG. 6.

Figure 6:
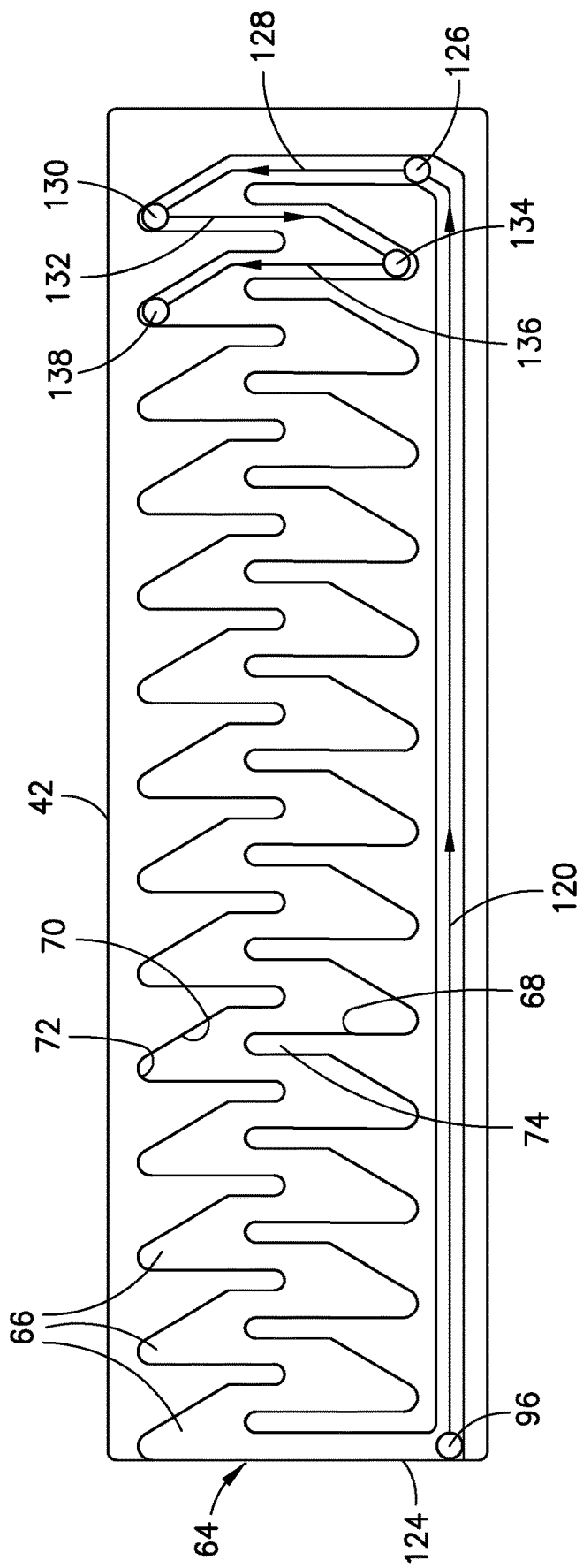
FIG. 6 is a schematic showing a track system of the plunger designed in accordance with the present invention shown in FIG. 2.

FIG. 6 is a schematic showing the track 64 of the plunger 40 designed in accordance with the present invention shown in FIG. 2. It shows the track 64 in greater detail and also shows an optional bypass track 120 that can be used to assemble the syringe 110 in one embodiment. In an embodiment wherein the pin 96 is fixed in the through hole 98 prior to assembly of the syringe 110, the bypass track 120 is used to allow the plunger advancer 90 to be inserted into the plunger 40. In this assembly method, the pin 96 is inserted into the plunger 40 at a pin entry point 124 in the bypass track 120 and then the shaft 94 can be inserted fully into the plunger 40 with the pin 96 riding in the bypass track 120. When the shaft 94 is fully inserted in the plunger 40, the pin 96 will be located at a pin rest point 126 at the start of the track 64. In the embodiment not having a bypass track 120 the pin 96 is inserted in the through hole 62 and the through hole 98 when they are aligned. In the embodiment having a bypass channel 120, the bypass channel 120 is only accessible at the start of use of the syringe 110 in a micro-dosing syringe pump. Once delivery of doses is begun, the bypass channel 120 can no longer be accessed by the pin 96. If at the start of dosing, the motor rotates the gear 92 in the incorrect direction the pin 96 will be pegged into the pin rest point 126 and the plunger 40 will rotate in place with no dose being dispensed. The dosing will begin after the gear 92 rotation is reversed as described herein. In both embodiments, the pin 96 is located at the pin rest point 126 prior to a first dose of a medicament being dispensed from the reservoir 10.

The mechanics of the syringe 110 will be described with specific reference to FIG. 6. For ease of description, movement in an upward direction in FIG. 6 will be described as clockwise rotation of the shaft 94 and movement in a downward direction in FIG. 6 will be described as counterclockwise rotation of the shaft 94; however, one of skill in the art would understand that it could be described in the reverse orientation. Referring back to FIG. 6, when a first dose is dispensed the gear 92 is rotated in a clockwise direction and the pin 96 is driven from the pin rest point 126 along a first travel path 128 to an end point 130 of the first travel path 128. The first travel path 128 includes the straight run 68 followed by the camming run 70 and the end point 72. Because of the shape of the camming run 70, a downward slope away from the piston 48, as the pin 96 is rotated it will drive the plunger 40 into the reservoir 10 as the pin 96 rotates against the camming run 70. This occurs because the pin 96 is always in the same rotational plane during rotation of the pin 96 irrespective of the direction of rotation and the camming runs 70 have a slope away from the piston 48. Thus, the plunger advancer 90 cannot move longitudinally so rotation of the pin 96 against the camming run 70 telescopes the plunger 40 away from the gear 92 and into the reservoir 10. Once the pin 96 reaches the end point 72 if the gear 92 were to be further rotated in the clockwise direction there would be no further advancement of the plunger 40 into the reservoir 10. Instead, the plunger 40 would simply rotate in position inside the reservoir 10. This is a safety feature that prevents excess dosing in a situation wherein the micro-dosing syringe pump motor, not shown, has a malfunction and continues to rotate the gear 92 in a clockwise rotation. In summary, rotation of the gear 92 in a first direction advances the plunger 40 a first distance into the reservoir 10 and delivers a first dose. In a normal function, the next dose is delivered by reversing the rotation of the gear 92 to rotate it in a counterclockwise manner. When the gear 92 is driven in the counterclockwise rotation the pin 96 moves from pin position 130 to pin position 134 along the second dose pin travel path 132. The second dose travel path 132 includes an initial straight run 68 followed by a camming run 70, which ends in an end point 72. Again, in a runaway motor malfunction, once the pin 96 reaches pin position 134 continued rotation in a counterclockwise rotation will not advance another dose and the plunger 40 will simply spin the reservoir 10 without further advancement. Therefore, rotation of the gear 92 in a second direction, opposite the first direction, advances the plunger 40 a further distance into the reservoir 10 to deliver a second dose. In delivery of the third dose, the rotation of the gear 92 is alternated back to a counterclockwise direction and the pin 96 is moved from pin position 134 to pin position 138 along the third dose travel path 136. The third dose travel path 136 includes a straight run 68 followed by a camming run 70 and an end point 72. As can be seen continuing to reverse the rotational direction of the gear 92 after each dose will continue to advance the plunger 40 further and further into the reservoir 10 until the pin 96 reaches the end of the track 64 at the open end 44 of the plunger 40. Thus, one can see how the pin 96 moves through the zigzag pattern of the track 64 to deliver a dose with each zig and each zag and each dose being the same. The length of the camming run 70 relative to the width of the separation wall 74 ensures that once the pin 96 travels down the camming run 70 to the end point 72 of a slot 66 and the rotation of the gear 92 is reversed to deliver the next dose, the pin 96 cannot jump back up to the straight run 68 of the previously traveled slot 66. As discussed above, the slots 66 can have other shapes besides those shown in the figures so long as the slot shape includes a camming run 70 shape that drives the plunger 40 into the reservoir 10 as the gear 92 is driven in one rotational direction and then further into the reservoir 10 as the gear 92 is driven in an opposite rotational direction. As can be understood from this description, the plunger 40 telescopes further away from the gear 92 and into the reservoir 10 as the syringe 110 is used as described with alternating rotational directions applied to the gear 92. Each rotational direction change drives the plunger 40 further into the reservoir 10. Once the pin 96 reaches the end of the track 64 the plunger 40 is no longer able to be driven further into the reservoir 10 and any rotation of gear 92 just spins the plunger 40 in place within the reservoir 10. The relative positions of the reservoir 10 and the plunger advancer 90 do not change inside the micro-dosing syringe pump during use. The plunger advancer 90 only rotates back and forth with no longitudinal movement and likewise the reservoir 10 has no longitudinal movement.

As described the syringe 110 according to the present invention is designed to be used in a micro-dosing syringe pump, which are known to those of skill in the art. The present invention prevents any possibility of excess dosing of a medicament caused by a runaway motor in the syringe pump continuing to drive the gear 92 in a given rotational direction. This safety feature is a result of the mechanical design of the track 64 and thus the safety feature is always "on" in this syringe 110. Micro-dosing syringe pumps are commonly used to deliver medicaments such as, for example, insulin, other hormones, chemotherapy medicaments, antibiotics and pain relievers. Thus, the need to ensure accurate dosing is critical and this invention ensures that occurs. The rotational drive direction of motors found in such micro-dosing syringe pumps can be controlled by switching electrical signals and via software as is known in the art. The present invention is also advantageous because it eliminates the need for fine motor controls in the syringe pump and any need for a motor encoder system. A preferred feature of the present invention is to include some over rotation of the pin 96 on each dosing cycle once it reaches the end point 72 of each slot 66. This ensures that the pin 96 reaches the end point 72 on each rotation for a proper dosing. It also helps in the manufacturing process to allow for manufacturing tolerances that do not need to be as tightly controlled and it reduces the need to precisely control when rotation is reversed. The micro-dosing syringe pump will include software to control the function of the motor, monitor the dosing required and the dosing dispensed. For example, in some instances the software may direct the motor to engage in three dosing cycles in a row to deliver the proper amount of a medicament. In other instances, a single dose at a time might be delivered. In addition, the software might direct the motor to deliver a dose every hour. Such dosing control by software is known to those of skill in the art and will not be described further herein.

The foregoing disclosure has been described in accordance with the relevant legal standards, thus the description is exemplary rather than limiting in nature. In some example embodiments, well-known processes, well-known device structures, and well-known technologies are not described in detail. Variations and modifications to the disclosed embodiment may become apparent to those skilled in the art and do come within the scope of the disclosure. Accordingly, the scope of legal protection afforded this disclosure can only be determined by studying the following claims.

We claim:
1. A syringe comprising:
a reservoir having an outlet port;
a plunger having a track, said plunger received inside a portion of said reservoir;
a plunger driver comprising a gear connected to one end of a shaft and a pin located adjacent an opposite end of said shaft, said plunger driver received inside said plunger with said pin located inside and engaging said track; and whereby rotation of said gear in a first direction advances said plunger into said reservoir a first distance as said pin travels in said track and rotation of said gear in a second direction opposite said first direction advances said plunger a further distance into said reservoir as said pin travels in said track.

2. The syringe as recited in claim 1, wherein said track comprises a plurality of slots.

3. The syringe as recited in claim 2, wherein said pin travels in a first of said plurality of slots when said gear is rotated in said first direction and in a second of said plurality of slots when said gear is rotated in said second direction.

4. The syringe as recited in claim 2, wherein each of said slots includes a straight run, a camming run and an end point.

5. The syringe as recited in claim 2, wherein said track and said plurality of slots are cut into an interior wall of said plunger.

6. The syringe as recited in claim 2, wherein each of said plurality of slots is separated from an adjacent slot by a separation wall.

7. The syringe as recited in claim 2, wherein said plurality of slots form a zigzag pattern in said track.

8. The syringe as recited in claim 1, wherein said plunger further includes a bypass track that is in communication with said track.

9. The syringe as recited in claim 1, wherein said plunger further includes a piston having an O-ring.

10. The syringe as recited in claim 4, wherein said plunger further includes a piston and said camming run is sloped in a direction away from said piston.

11. The syringe as recited in claim 2, wherein said track and said plurality of slots are cut through a wall of said plunger.

12. A syringe comprising:
a reservoir having an outlet port;
a plunger having a track, said track comprising a plurality of slots, each of said slots comprising a straight run, a camming run and an end point, and said plunger received inside a portion of said reservoir;
a plunger driver comprising a gear connected to one end of a shaft and a pin located adjacent an opposite end of said shaft, said plunger driver received inside said plunger with said pin located inside and engaging said track; and whereby rotation of said gear in a first direction advances said plunger into said reservoir a first distance as said pin travels in a first of said plurality of slots and rotation of said gear in a second direction opposite said first direction advances said plunger a further distance into said reservoir as said pin travels in a second of said slots.

13. The syringe as recited in claim 12, wherein said first of said plurality of slots is adjacent to said second of said plurality of slots.

14. The syringe as recited in claim 12, wherein said track and said plurality of slots are cut into an interior wall of said plunger.

15. The syringe as recited in claim 12, wherein each of said plurality of slots is separated from an adjacent slot by a separation wall.

16. The syringe as recited in claim 12, wherein said plurality of slots form a zigzag pattern in said track.

17. The syringe as recited in claim 12, wherein said plunger further includes a bypass track that is in communication with said track.

18. The syringe as recited in claim 12, wherein said plunger further includes a piston having an O-ring.

19. The syringe as recited in claim 12, wherein said plunger further includes a piston and said camming run is sloped in a direction away from said piston.

20. The syringe as recited in claim 12, wherein said track and said plurality of slots are cut through a wall of said plunger.

\* \* \* \* \*